(12) United States Patent
Hildebrandt et al.

(10) Patent No.: US 6,342,594 B1
(45) Date of Patent: *Jan. 29, 2002

(54) NUCLEIC ACID WHICH IS UPREGULATED IN METASTATIC HUMAN TUMOR CELLS

(75) Inventors: Tobias Hildebrandt, Reutlingen (DE); Goosen Van Muijen, Nijmegen (NL); Ulrich Weidle, München (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/412,484

(22) Filed: Oct. 5, 1999

(30) Foreign Application Priority Data

Oct. 7, 1998 (EP) .............................................. 98118919

(51) Int. Cl.⁷ ............................................... C07H 21/04
(52) U.S. Cl. ...................... 536/23.5; 536/23.1; 530/350
(58) Field of Search ............................... 536/23.1, 23.5, 536/24.1, 24.33; 435/320.1; 530/352

(56) References Cited

U.S. PATENT DOCUMENTS 5,539,096 A 7/1996 Babaï et al.

FOREIGN PATENT DOCUMENTS

WO  WO 96/21042 A  7/1996

OTHER PUBLICATIONS

Funke et al Genomics 53:146–154, Oct. 23, 1998.*
Promege Catalog, Section 3, Nucleic acids, 1993/94.
EMBL/GENBANK DATABASES, Accesson No. W95859, Hillier et al., "The WashU–Merck EST Project", July 18, 1996.

Hashimoto et al., Cancer Research, 56(22):5266–5271 (Nov. 15, 1996).

Christensen et al., Cancer Research, 58(6):1238–1244 (Mar. 15, 1998).

Schwabe et al., Journal of Molecular Medicine (Berlin), 76(6):B20 (May 1998) (see abstract No. P–70).

Dang et al., The Journal of Biological Chemistry, 264(30):18019–18023 (Oct. 25, 1989).

Dingwall et al., The Journal of Cell Biology, 107:841–849 (1988).

Guo et al., Biochemistry, 36(47):14447–14455 (1997).

Johnson et al., Proc. Natl. Acad. Sci. USA, 91:12823–12827 (Dec. 1994).

Kouzarides et al., Nature, 340:568–571 (Aug. 17, 1989).

Neuberg et al., Nature, 341:243–245 (Sep. 21, 1989).

Streit et al., Recent Results in Cancer Research, 142:19–50 (1996).

Van Muijen et al., Clin. Expl. Metastasis, 9(3):259–272 (1991).

Versteeg et al., The EMBO Journal, 7(4):1023–1029 (1988).

Hildebrandt et al., Anticancer Research, 19:525–530 (1999).

* cited by examiner

*Primary Examiner*—Sheela Huff
*Assistant Examiner*—Larry R. Helms
(74) *Attorney, Agent, or Firm*—George W. Johnston; Patricia S. Rocha-Tramaloni; Eileen M. Ebel

(57) ABSTRACT

A nucleic acid molecule (URIM) with the nucleic acid sequence SEQ ID NO:1 is capable of inducing tumor progression and/or metastasis. The URIM protein of SEQ ID NO:2 is also provided. A process for determining whether a tumor sample has metastatic potential is provided.

4 Claims, 5 Drawing Sheets

Fig. 1
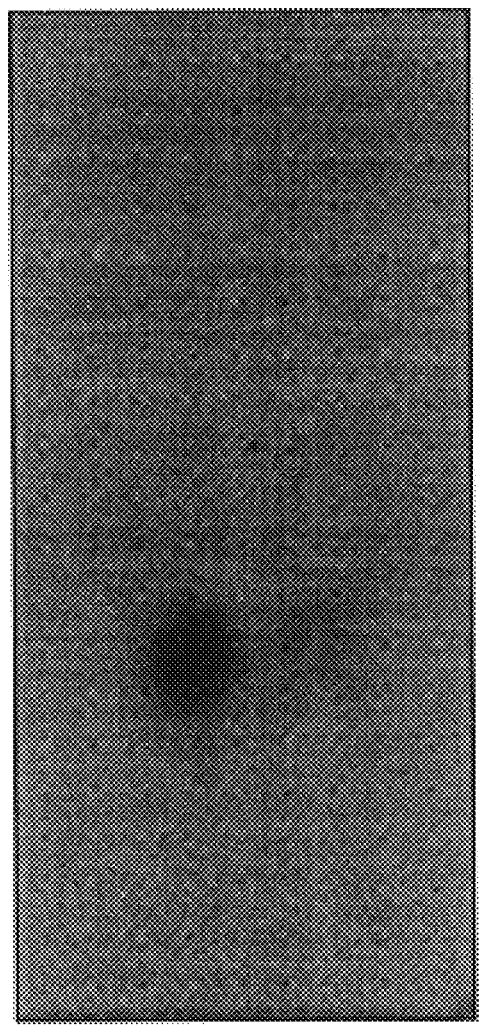
← 0.9 kb
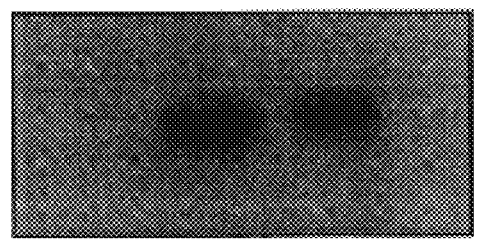
← β-actin

Fig. 2

```
  1 gagggtagccATGACGGCCTCCGTGCTGCGAAGTATCTCGCTAGCCCTGCGCCCGACTAG   60
  1           M  T  A  S  V  L  R  S  I  S  L  A  L  R  P  T  S    17

61 CGGGCTTCTGGGAACTTGGCAGACGCAGCTTAGAGAGACTCACCAGCGAGCGTCATTGTT  120
 18  G  L  L  G  T  W  Q  T  Q  L  R  E  T  H  Q  R  A  S  L  L   37

121 GTCTTTCTGGGAACTCATTCCCATGAGATCAGAACCTCTTCGAAAAAAGAAGAAGGTAGA  180
 38  S  F  W  E  L  I  P  M  R  S  E  P  L  R  K  K  K  K  V  D   57

181 TCCTAAAAAAGACCAAGAAGCAAAGGAGCGCTTGAAAAGGAAGATCCGAAAACTGGAAAA  240
 58  P  K  K  D  Q  E  A  K  E  R  L  K  R  K  I  R  K  L  E  K   77

241 GGCTACTCAAGAGCTAATTCCTATTGAAGATTTTATTACCCCTCTAAAGTTCTTGGATAA  300
 78  A  T  Q  E  L  I  P  I  E  D  F  I  T  P  L  K  F  L  D  K   97

301 AGCAAGAGAGCGGCCTCAGGTGGAGCTCACCTTTGAGGAGACTGAGAGGAGAGCTCTGCT  360
 98  A  R  E  R  P  Q  V  E  L  T  F  E  E  T  E  R  R  A  L  L  117

361 TCTGAAGAAGTGGTCCTTGTACAAGCAGCAAGAGCGTAAGATGGAGAGGGACACCATCAG  420
118  L  K  K  W  S  L  Y  K  Q  Q  E  R  K  M  E  R  D  T  I  R  137

421 GGCTATGCTAGAAGCCCAGCAGGAAGCTCTGGAGGAACTGCAACTGGAATCCCCGAAGCT  480
138  A  M  L  E  A  Q  Q  E  A  L  E  E  L  Q  L  E  S  P  K  L  157

481 CCATGCTGAGGCCATCAAGCGGGATCCTAACCTGTTCCCCTTTGAGAAGGAAGGGCCACA  540
158  H  A  E  A  I  K  R  D  P  N  L  F  P  F  E  K  E  G  P  H  177

541 TTACACACCACCGATCCCTAACTACCAACCCCCTGAAGGCAGGTACAATGACATCACCAA  600
178  Y  T  P  P  I  P  N  Y  Q  P  P  E  G  R  Y  N  D  I  T  K  197

601 GGTGTACACACAAGTGGAGTTTAAGAGATAGacttgcaggctgctatccttaacatgctg  660
198  V  Y  T  Q  V  E  F  K  R  *                                217

661 ccctgagagtaggaatgaccagggttcaagtctgccttccacagaatcaggcatgctgt   720

721 taataaatctggtttaatcaaaaaaaaaaagcttc   755
```

NUCLEIC ACID WHICH IS UPREGULATED IN METASTATIC HUMAN TUMOR CELLS

BACKGROUND OF THE INVENTION

In order for metastasis of cancer to occur, several hurdles must be overcome, such as degradation of the extracellular matrix and basal membrane, intra- and extravasation of vessels of the blood and of the lymphatic system, escape by the attack of the immune system, and homing and colonization of distant organs (Pardee, A. B., Advances in Cancer Res. 65 (1994) 213–227; Ponta, H., et al., Biochem. Biophys. Acta 1198 (1994) 1–10). A further level of complexity is achieved in that different types of cancers make use of different molecular mechanisms for metastasis and exhibit different tropism of metastasis.

Metastasizing and non-metastasizing human melanoma cell lines have been important tools in identifying differentially expressed genes and for investigation of their role in metastasis (Weterman, M .A .J., et al., Cancer Res. 52 (1992) 1291–1296; Weterman, M. A. J., et al., Int. J. Cancer 53 (1993) 278–284; Van Groningen, J. M., et al., Cancer Res. 55 (1995) 6237–6243; Weterman, M. A. J. , et al., Int. J. Cancer 60 (1995) 73–81; van Muijen, G. N. P., et al., Int. J. Cancer 48 (1991) 85–91; van Muijen, G. N. P., et al., Clin. Exp. Metastasis 9 (1991) 259–272). Cell adhesion molecules play an important role in the invasion, dissemination, extravasation and lodging of tumor cells. The interaction of disseminated tumor cells with endothelium and tissue stroma is supposed to be one of the critical steps in tumor progression and metastasis formation (Ebnet, K., et al., Annu. Rev. Immunol. 14 (1996) 155–177; Varner, J. A., and Cheresh, D. A., Curr. Opin. Cell Biol. 8 (1996) 724–730; Albelda, S. M., Lab. Invest. 68 (1993)4–17).

SUMMARY OF THE INVENTION

In accordance with the present invetion, a protein, termed URIM, is provided which is upregulated in metastatic cancer cells as compared to their non-metastatic counterparts. URIM may be involved in promotion of several steps of the metastatic cascade. The URIM gene codes for a polypeptide of SEQ ID NO:2.

The present invention provides an isolated nucleic acid which is upregulated in metastatic tumor cells and which codes for a polypeptide which induces tumor progression or metastasis, the nucleic acid being selected from the group consisting of:

(a) SEQ ID NO: 1;
(b) a nucleic acid sequence which hybridizes under stringent conditions with a nucleic acid probe selected from the group consisting of the complementary sequence of (a), SEQ ID NO:6 and SEQ ID NO:7;
(c) a nucleic acid sequence which, because of the degeneracy of the genetic code, is not a sequence of (a) or (b), but which codes for a polypeptide having exactly the same amino acid sequence as a polypeptide encoded by a sequence of (a) or (b); and
(d) a nucleic acid sequence which is a fragment of any of the sequences of (a), (b) or (c).

The present invention further provides a purified and isolated polypeptide having a sequence of SEQ ID NO:2.

The present invention further provies a process for detecting the presence or absence of at least one specific nucleic acid or mixture of nucleic acids, or distinguishing between two different sequences in said sample, wherein the sample is suspected of containing said sequence or sequences, which process comprises the following steps in order:

(a) incubating said sample under stringent hybridization conditions with a nucleic acid probe which is selected from the group consisting of;
  (i) a nucleic acid sequence taken from the group consisting of SEQ ID NO: 1, SEQ ID NO:6 and SEQ ID NO:7;
  (ii) a nucleic acid sequence which is exactly complementary to any nucleic acid sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining whether said hybridization has occurred.

Moreover, the present invention provides a process for determining whether or not a cancer cell-containing test sample has potential for tumor progression or metastasis, wherein the test sample and a cancer cell-containing sample wherein is free from metastasis are obtained from the same individual or different individuals of the same species, which process comprises the following steps:

(a) incubating each respective sample under stringent hybridization conditions with a nucleic acid probe which is selected from the group consisting of:
  (i) a nucleic acid sequence taken from the group consisting of SEQ ID NO: 1, SEQ ID NO:6 and SEQ ID NO:7;
  (ii) a nucleic acid sequence which is exactly complementary to any nucleic acid sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining the approximate amount of hybridization of each respective sample with said probe, and
(c) comparing the approximate amount of hybridization of the test sample to an approximate amount of hybridization of the sample which is free from metastasis, to identify whether or not the test sample contains a greater amount of the specific nucleic acid or mixture of nucleic acids than does the sample which is free from metastasis.

Furthermore, the present invention provides an isolated nucleic acid which inhibits a nucleic acid in inducing tumor progression and metastasis, said isolated nucleic acid having a sequence selected from the group consisting of:

(a) a nucleic acid sequence which is exactly complementary to SEQ ID NO: 1; and
(b) a nucleic acid sequence which hybridizes under stringent conditions with the sequence of (a).

DETAILED DESCRIPTION OF THE INVENTION

The present invention provides the new gene URIM (Up-Regulated In Metastasis), a protein coded thereby, and use of the URIM gene for diagnostics and therapeutics, especially in the field of cancer. In particular, the invention involves the identification of said gene URIM in mammalian, especially in malignant tumor cells. The invention also relates to diagnosis of the metastatic and progression potential of tumor cells and to gene therapy methods to inhibit URIM in its function in tumor cells.

The invention comprises a nucleic acid molecule (URIM) which has upregulated expression in metastatic tumor cells and which is capable of inducing tumor progression and/or metastasis, especially in malignant melanoma and mammary carcinoma cells. The nucleic acid (URIM) has the sequence SEQ ID NO:1 or it is a nucleic acid which, because of the degeneracy of the genetic code, differs from SEQ ID NO:1, but which encodes the amino acid sequence encoded by the nucleic acid of SEQ ID NO:1.

The invention further comprises a recombinant polypeptide which is coded by the nucleic acid sequences according to the invention, preferably by the DNA sequence shown in SEQ ID NO:1.

The isolated URIM polypeptide can occur in natural allelic variations which differ from individual to individual. Such variations of the amino acids are usually amino acid substitutions. However, they may also be deletions, insertions or additions of amino acids to the total sequence. The URIM protein according to the invention—depending, both in respect of the extent and type, on the cell and cell type in which it is expressed—can be in glycosylated or non-glycosylated form. Polypeptides with metastatic activity can be identified by transfection of URIM-negative non-metastasizing tumor cells with expression vectors for URIM, establishment of stable transfectants and evaluation of in vitro invasiveness in Matrigel invasion assays and their metastatic capacity after xenografting into nude mice.

"Polypeptide with URIM activity or URIM" means also proteins with minor amino acid variations but with substantially the same URIM activity. Substantially the same means that the activities are of the same biological properties and the polypeptides show at least 90% homology (identity) in amino acid sequence.

The term "nucleic acid molecule or nucleic acid" denotes a polynucleotide molecule which can be, for example, a DNA, RNA, or derivatized active DNA or RNA. DNA and/or RNA molecules are preferred, however.

The term "hybridize under stringent conditions" means that two nucleic acid fragments are capable of hybridization to one another under standard hybridization conditions described in Sambrook et al., Molecular Cloning: A Laboratory Manual (1989) Cold Spring Harbor Laboratory Press, New York, USA. More specifically, "stringent conditions" as used herein refer to hybridization in 6.0×SSC at about 45° C., followed by a wash. This wash can be with 2.0×SSC at 50° C. Preferably, hybridization is performed using the commercially available Express Hyb™ Hybridization Solution of Clontech, which is a non-viscous solution containing no salmon sperm DNA. The stringency of the salt concentration in the wash step can be selected, for example, from about 2.0×SSC at 50° C., for low stringency, to about 0.2×SSC at 50° C., for high stringency. In addition, the temperature in the wash step can be increased from low stringency conditions at room temperatures, about 22° C., to high stringency conditions at about 65° C.

The phrase "nucleic acid or polypeptide" as used throughout this application refers to a nucleic acid or polypeptide having a URIM activity which is substantially free of cellular material or culture medium when produced by recombinant DNA techniques, or substantially free of chemical precursors or other chemicals when synthesized chemically. Such a nucleic acid is preferably free of sequences which naturally flank the nucleic acid (i.e. sequences located at the 5' and the 3' ends of the nucleic acid) in the organism from which the nucleic acid is derived.

URIM can be purified after recombinant production by affinity chromatography using known protein purification techniques, including immunoprecipitation, gel filtration, ion exchange chromatography, chromatofocussing, isoelectric focussing, selective precipitation, electrophoresis, or the like.

The polypeptides according to the invention can be produced by recombinant means, or synthetically. Non-glycosylated URIM polypeptide is obtained when it is produced recombinantly in prokaryotes. With the aid of the nucleic acid sequences provided by the invention it is possible to search for the URIM gene or its variants in genomes of any desired cells (e.g. apart from human cells, also in cells of other mammals), to identify these and to isolate the desired gene coding for the URIM protein. Such processes and suitable hybridization conditions are known to a person skilled in the art and are described, for example, by Sambrook et al., Molecular Cloning: A Laboratory Manual (1989) Cold Spring Harbor Laboratory Press, New York, USA, and Hames, B. D., Higgins, S. G., Nucleic Acid Hybridisation—A Practical Approach (1985) IRL Press, Oxford, England. In this case the standard protocols described in these publications are usually used for the experiments.

With the aid of such nucleic acids coding for a URIM protein, the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as, e.g., *E. coli* as a prokaryotic host cell or *Saccharomyces cerevisiae*, Teratocarcinoma cell line PA-1 sc 9117 (Büttner et al., Mol. Cell. Biol. 11 (1991) 3573–3583), insect cells, CHO or COS cells as eukaryotic host cells and the transformed or transduced host cells are cultured under conditions which allow expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary if it is not found in soluble form in the cell culture.

The invention further comprises recombinant expression vectors which are suitable for the expression of URIM, recombinant host cells transfected with such expression vectors, as well as a process for the recombinant production of a protein which is encoded by the URIM gene.

The invention further comprises a method for detecting a nucleic acid molecule of gene URIM, comprising incubating a sample (e.g., body fluids such as blood, cell lysates) with the isolated nucleic acid molecule according to the invention and determining hybridization under stringent conditions of said isolated nucleic acid molecule to a target nucleic acid molecule for determination of presence of a nucleic acid molecule which is the URIM gene and therefore a method for the identification of the metastatic potential and/or progression of tumor cells.

To determine whether a cancer cell-containing test sample has potential for tumor progression or metastasis, the approximate amount of hybridization of the isolated nucleic acid with the target nucleic acid or nucleic acids is determined. The approximate amount of hybridization need not be determined quantitatively, although a quantitative determination is encompassed by the present invention. Typically, the approximate amount of hybridization is determined qualitatively, for example, by a sight inspection upon detecting hybridization. For example, if a gel is used to resolve labelled nucleic acid which hybridizes to target nucleic acid in the sample, the resulting band can be inspected visually. When performing a hybridization of isolated nucleic acid in a cancer-containing sample which is free from metastasis from an individual of the same species, the same protocol is followed. One can compare the approximate amount of hybridization in the test sample to the approximate amount of hybridization in the sample free from metastasis, to identify whether or not the test sample contains a greater amount of the target nucleic acid or nucleic acids than does the sample which is free from metastasis. For visual inspection in particular, it is recommended that an appreciable difference by visualized to assess that the test sample contains a greater amount of the target nucleic acid or nucleic acids.

As is shown in accordance with the present invention, the URIM nucleic acid is present in a greater amount in a metastasized tumor sample than in a sample free from metastasis. A test sample having potential for tumor progression or metastasis will have a greater amount of the URIM nucleic acid of the present invention than does a cancer cell sample which is free from metastasis. To identify a test sample as containing upregulated URIM nucleic acid, i.e., wherein the cancer cells have potential for tumor progression or metastasis, it is preferable that the test sample have an approximate amount of URIM nucleic acid which is appreciably greater that the approximate amount in a non-metastasigned sample. For example, a test sample having an upregulated URIM gene may have approximately 15- to approximatly 60-fold greater amount of URIM gene than a non-metastasized sample.

On the basis of the nucleic acids provided by the invention it is possible to provide a test which can be used to detect nucleic acids with upregulated expression in metastatic human tumor cells. Such a test can be carried out by means of nucleic acid diagnostics. In this case the sample to be examined is contacted with a probe that is selected from the group comprising
    a) the nucleic acid sequence shown in SEQ ID NO:1, the nucleic acid sequence shown in SEQ ID NO:6, SEQ ID NO:7 or a nucleic acid sequence which is complementary to one of these nucleic acid sequences, and
    b) nucleic acids which hybridize under stringent conditions with one of the nucleic acids from a), wherein
the nucleic acid probe is incubated with the nucleic acid of the sample and the hybridization is detected optionally by means of a further binding partner for the nucleic acid of the sample and/or the nucleic acid probe. For obtaining a nucleic acid by hybridization in accordance with b), it is preferable to hybridize to the probe shown in SEQ ID NO:6 or a sequence complementary thereto. SEQ ID NO:6 corresponds to nucleotide numbers 8 to 670 of SEQ ID NO:1. Hybridization between the probe used and nucleic acids from the sample indicates the presence of the RNA of such proteins.

Methods of hybridization of a probe and a nucleic acid are known to a person skilled in the art and are described, for example, in WO 89/06698, EP-A 0 200 362, U.S. Pat. No. 2,915,082, EP-A 0 063 879, EP-A 0 173 251, EP-A 0 128 018.

In a preferred embodiment of the invention the coding nucleic acid of the sample is amplified before the test, for example by means of the known PCR technique. Usually a derivatized (labeled) nucleic acid probe is used within the framework of nucleic acid diagnostics. This probe is contacted with a denatured DNA or RNA from the sample which is bound to a carrier and in this process the temperature, ionic strength, pH and other buffer conditions are selected—depending on the length and composition of the nucleic acid probe and the resulting melting temperature of the expected hybrid—such that the labeled DNA or RNA can bind to homologous DNA or RNA (hybridization see also Wahl, G. M., et al., Proc. Natl. Acad. Sci. USA 76 (1979) 3683–3687). Suitable carriers are membranes or carrier materials based on nitrocellulose (e.g., Schleicher and Schüll, BA 85, Amersham Hybond, C.), strengthened or bound nitrocellulose in powder form or nylon membranes derivatized with various functional groups (e.g., nitro groups) (e.g., Schleicher and Schüll, Nytran; NEN, Gene Screen; Amersham Hybond M.; Pall Biodyne).

Hybridizing DNA or RNA is then detected by incubating the carrier with an antibody or antibody fragment after thorough washing and saturation to prevent unspecific binding. The antibody or the antibody fragment is directed towards the substance incorporated during hybridization to the nucleic acid probe. The antibody is in turn labeled. However, it is also possible to use a directly labeled DNA. After incubation with the antibodies it is washed again in order to only detect specifically bound antibody conjugates. The determination is then carried out according to known methods by means of the label on the antibody or the antibody fragment.

The detection of the expression can be carried out for example as:
    in situ hybridization with fixed whole cells, with fixed tissue smears and isolated metaphase chromosomes,
    colony hybridization (cells) and plaque hybridization (phages and viruses),
    Southern hybridization (DNA detection),
    Northern hybridization (RNA detection),
    serum analysis (e.g., cell type analysis of cells in the serum by slot-blot analysis),
    after amplification (e.g., PCR technique).

Therefore the invention also includes a method for the detection of the metastatic potential of melanoma and mammary carcinoma cells, comprising
    a) incubating a sample of body fluid of a patient suffering from cancer, of melanoma cancer cells, of mammary carcinoma cells, or of a cell extract or cell culture supernatants of said cancer cells, whereby said sample contains nucleic acids with a nucleic acid probe which is selected from the group consisting of
        (i) the nucleic acid shown in SEQ ID NO:1, SEQ ID NO:6, or SEQ ID NO:7, or a nucleic acid which is complementary to one of these nucleic acid sequences, and
        (ii) nucleic acids which hybridize with one of the nucleic acids from (i) and
    b) detecting hybridization by means of a further binding partner of the nucleic acid of the sample and/or the nucleic acid probe or by X-ray radiography.

Preferably the nucleic acid probe is incubated with the nucleic acid of the sample and the hybridization is detected optionally by means of a further binding partner for the nucleic acid of the sample and/or the nucleic acid probe.

The nucleic acids according to the invention are hence valuable prognostic markers in the diagnosis of the metastatic and progression potential of tumor cells of a patient.

The invention further comprises a method for producing a protein whose expression is correlated with tumor metastasis, by expressing an exogenous DNA in prokaryotic or eukaryotic host cells and isolation of the desired protein, wherein the protein is coded by the nucleic acid molecules according to the invention, preferably by the DNA sequence shown in SEQ ID NO:1.

The protein can be isolated from the cells or the culture supernatant and purified by chromatographic means, preferably by ion exchange chromatography, affinity chromatography and/or reverse phase HPLC.

The invention further comprises an isolated protein according to the invention which is encoded by a nucleic acid molecule according to the invention, preferably having the nucleotide sequence set forth in SEQ ID NO:1.

The present invention relates to the cloning and characterization of the gene URIM, which is especially characterized as a tumor progression gene, and as an upregulated gene indicative for metastatic potential of melanoma cells. The function of the gene according to the invention (URIM) is to promote loss of contact inhibition and anchorage dependence in tumor cells and to promote other essential steps of the metastatic cascade. Therefore the expression of URIM gene correlates with a more aggressive behavior of the tumor cells and also with the potential of the formation of metastasis.

According to the invention inhibitors for the expression of URIM (e.g., antisense nucleotides) can be used to inhibit tumor progression/metastasis, preferably of malignant melanomas and mammary carcinomas, in vivo, preferably by somatic gene therapy.

Differential Display Technique applied to non-metastatic melanoma cell line 530 and metastatic melanoma cell line NMCL-1 resulted in identification of a transcript (URIM) which was at least 40 fold up-regulated in the metastatic cell line (FIG. 1). The corresponding cDNA encodes a newly identified protein composed of 206 aa with an isoelectric point of 10.4, a putative nuclear localization signal and a putative leucine zipper motif (FIG. 2). The high isoelectric point and the presence of a putative nuclear localization signal (Dingwall, C., et al., J. Cell Biol. 107 (1988) 841–849; Dang, C. V., and Lee, W. M., J. Biol. Chem. 264 (1989) 18019–18023) are compatible with nuclear localization of URIM. In addition, the presence of a putative leucine zipper motif (Neuberg, M., et al., Nature 341 (1989) 243–245; Kouzarides, T., and Ziff, E., Nature 340 (1989) 568–571) indicates interaction with proteins forming homo- or heterodimeric species. Leucine zipper motifs have been identified in several transcription factors such as c-fos, c-jun, ATF1, B-ATF, CREB, and USP (Gou, B., et al., Biochemistry 36 (1997) 14447–14455; Dorsey, M. J., et al., Oncogene 11 (1995) 2255–2265; Lu, T., and Sawadogo, M., J. Biol. Chem. 269 (1994) 30694–30700). Therefore, URIM might function as a nuclear adapter protein, as a transcription factor or as a co-activator of a transcription factor. Overexpression of a transcription factor might confer a selective advantage in the process of metastasis by modulating gene expression in favour of genes promoting metastasis. The oncogenic potential of transcription factors as well as truncated versions or fusion proteins derived thereof is well documented (Johnson, D. G., et al., Proc. Natl. Acad. Sci. USA 91 (1994) 12823–12828; Papavassiliou, A. G., Anticancer Res. 15 (1995) 891–894; Curran, T., J. Exp. Med. 168 (1992) 169–174; Birnbaum, M. J., et al., J. Cell Biochem. 66 (1997) 175–183). Ubiquitous expression of URIM in human tissues and cancer cell lines of different origin (FIG. 3A and B) is compatible with assumptions as discussed above. Surprisingly up to 17 fold overexpression of URIM message was found in three cell lines derived from bone marrow micrometastasis of mammary carcinoma patients and a mammary carcinoma cell line derived from ascites fluid compared to two cell lines derived from primary mammary carcinoma and a cell line representing normal mammary gland epithelium (FIG. 4). Steady-state levels of URIM mRNA in the cell line derived from normal mammary gland and two cell lines derived from primary mammary carcinoma were almost identical (FIG. 4). Since autologous pairs of cell lines were not available, our investigations correspond to a heterologous setting. It is improbable that the expression pattern observed has arisen just by co-incidence. It seems that a gene identified in a melanoma metastasis model also is associated or is even driving metastasis in a tumor of epithelial origin as shown here for mammary carcinoma. This extrapolation also has been shown for other genes involved in tumor dissemination such as urokinase, urokinase receptor, metalloproteinases, E-Cadherin, Scatter Factor and others (Streit, M., et al., Recent Results Cancer Res. 142 (1996) 19–50; Joseph, A., et al., J. Natl. Cancer Inst. 87 (1995) 372–377; Stefler-Stevenson, W. G., et al., Semin Cancer Biology 7 (1996) 147–154; Weidle, U. H., and König, B., Exp. Opin. Invest. Drugs 7 (1998) 391–403).

The invention further provides methods for identifying and isolation of antagonists of URIM or inhibitors for the expression of URIM (e.g. antisense nucleotides). Such antagonists or inhibitors can be used to inhibit tumor progression or metastasis and cause massive apoptosis of tumor cells in vivo.

According to the invention there are provided methods for identifying and isolation of compounds which have utility in the treatment of cancer, especially in inhibiting metastasis and related disorders. These methods include methods for modulating the expression of the polypeptides according to the invention, methods for identifying compounds which can selectively bind to the proteins according to the invention, and methods of identifying compounds which can modulate the activity of said polypeptides. The methods further include methods for modulating, preferably inhibiting, the transcription of URIM gene to mRNA, which preferably down-regulates the metastatic potential of a tumor cell. These methods can be conducted in vitro or in vivo and may make use of and establish cell lines and transgenic animal models of the invention.

A URIM antagonist is defined as a substance or compound which decreases or inhibits the biological activity of URIM, a polypeptide and/or inhibits the transcription or translation of URIM gene. In general, screening procedures for URIM antagonists involve contacting candidate substances with host cells in which invasiveness is mediated by expression of URIM under conditions favorable for measuring URIM activity.

URIM activity may be measured in several ways. Typically, the activation is apparent by a change in cell physiology, such as increased mobility and invasiveness in vitro, or by a change in the differentiation state, or by a change in cell metabolism leading to an increase of proliferation.

The URIM gene and protein of the invention can be used to identify and design drugs which interfere with proliferation and dissemination of tumor cells.

The following examples, references, sequence listing and figures are provided to aid the understanding of the present invention. It is understood that modifications can be made in the procedures set forth without departing from the spirit of the invention.

SEQ ID NO:1: cDNA and amino acid sequence of URIM.
SEQ ID NO:2: Amino acid of URIM.
SEQ ID NO:3: Primer GSP1.
SEQ ID NO:4: Primer GSP2.
SEQ ID NO:5: Primer AUAP.

SEQ ID NO:6: Probe.
SEQ ID NO:7: Probe.

DESCRIPTION OF THE FIGURES

FIG. 1 Northern blot analysis of differential expression of URIM mRNA in cell lines 530 and NMCL-1. Poly A+ RNA from cell lines NMCL-1 (panel a) and 530 (panel b) was electrophoresed on a denaturing 1% agarose formaldehyde gel, transferred to a positively charged nylon membrane and hybridized to a $^{32}$P-labelled fragment covering the 3' region of URIM cDNA having the sequence of SEQ ID NO:7. The blot was rehybridized to a human β-actin probe as an internal reference.

FIG. 2 Nucleotide and amino acid sequence of URIM cDNA. Large capitals refer to nts in the coding region, small capitals refer to nts in the 5' as well as in the 3' untranslated region of URIM cDNA. A CDS region is present from nucleotide 11 to 631. Encoded aa are displayed at the corresponding nts according to the single letter code for aa. The putative leucine zipper (□) and nuclear localization signal (■) are highlighted. A star indicates the translational stop codon.

Expression of URIM mRNA in selected tissues and tumor cell lines. FIG. 3A displays expression of URIM mRNA in selected tissues, in FIG. 3B expression in selected tumor cell lines is shown. Clontech filters with immobilized poly A+ RNA were hybridized with a $^{32}$P-labeled probe covering the 3' coding region of URIM cDNA (SEQ ID NO:7).

FIG. 3A. Lanes: a, heart; b, brain; c, placenta; d, lung; e, liver; f, skeletal muscle; g, kidney; h, pancreas; i, spleen; j, thymus; k, prostate;, testis; m, ovary; n, small intestine; o, colon; p, peripheral blood leukocytes.

FIG. 3B. Lanes: a, HL-60 cells; b, HeLa cells; c, K562 cells; d, MOLT 4 cells; e, Raji cells; f, SW480 cells; g, A540 cells; h, G361 cells.

Lanes: a, human mammary epithelial cells (HMEC); b, cell line P1 derived from primary mammary carcinoma; c, cell line P2 derived from primary mammary carcinoma; d, cell line BM1, derived from bone marrow micrometastasis; e, cell line BM2, derived from bone marrow micrometastasis; f, cell line BM3, derived from bone marrow micrometastasis; g, cell line A1, derived from ascites fluid of a patient with metastastic breast cancer.

EXAMPLE 1

Materials and Methods
Differential Expression of a 0.9 kb mRNA in Cell Lines 530 and NMCL-1

Figure 3:
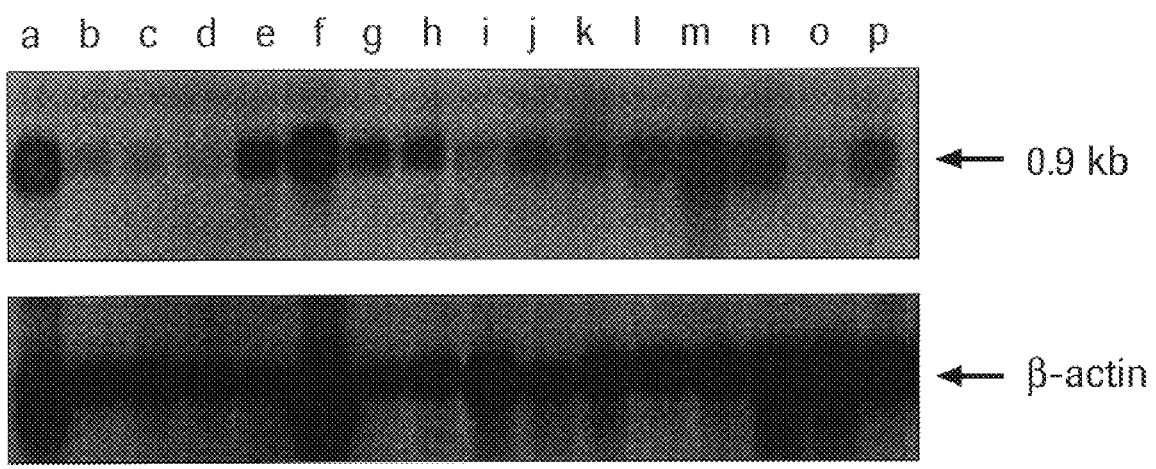
FIGS. 3A and 3B
Figure 3:
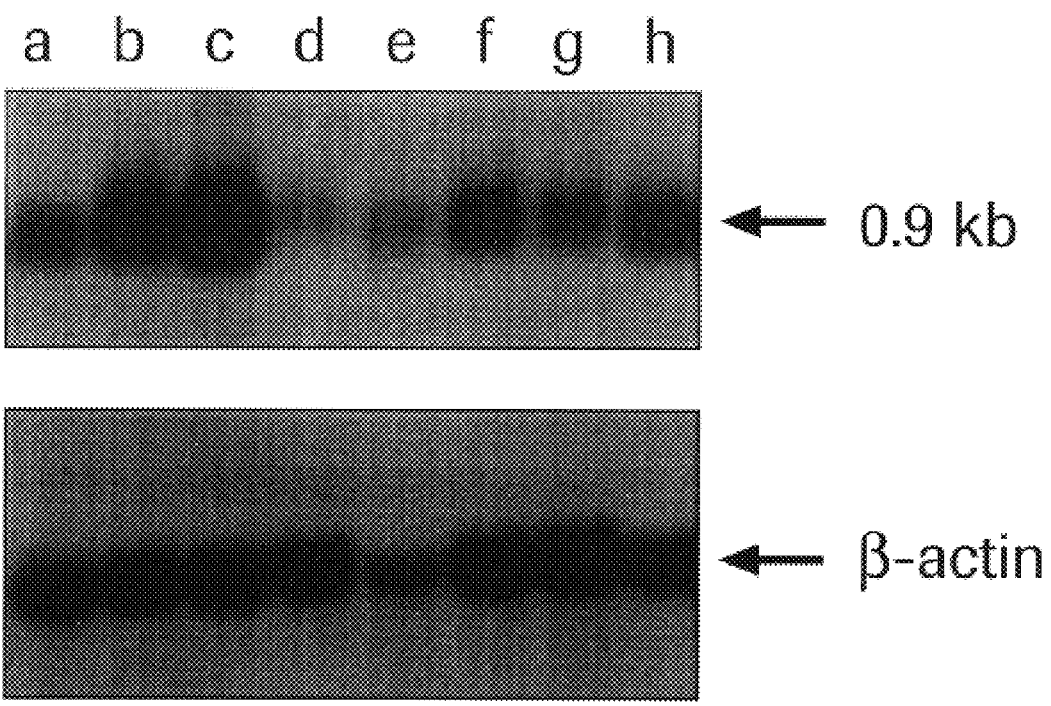

Cell line NMCL-1 was derived from a surgically removed melanoma metastasis which maintains its metastasizing properties after xenografting into nude mice. Cell line 530 was also derived from cutaneous melanoma but does not metastasize after xenografting into nude mice. In order to identify genes associated with and/or driving metastasis the "Differential Display Technique" was used for comparison of the transcriptional pattern of these two cell lines. A 0.9 kb transcript was detected whose steady-state level was 40 fold increased in the metastasizing cell line NMCL-1 (FIG. 1).
Expression of URIM in Normal Tissues and in Tumor Cell Lines Expression of URIM in normal tissues and in tumor cell lines was investigated by Northern blotting as displayed in FIG. 3. URIM mRNA was found in all tissues examined albeit at different levels. Low levels of URIM are expressed in brain, placenta, lung, spleen and colon (FIG. 3A, lanes b, c, d, i and o). High levels of URIM were detected in heart, liver, skeletal muscle, kidney, pancreas, thymus, prostate, testis, ovary, small intestine and peripheral blood leukocytes (FIG. 3A, lanes a, e, f, g, h, j, k, l, m, n, p). FIG. 3B reveals that URIM is expressed at high levels in cancer cell lines of different origin, such as promyelocytic leukemia cell line HL-60 (lane a), carcinoma cell line HeLa S3 (lane b), chronic myelogenous leukemia cell line K-562 (lane c), lymphoblastic leukemia cell line MOLT-4 (lane d), Burkitt's lymphoma cell line Raji (lane e), colorectal adenocarcinoma cell line SW480 (lane f), lung carcinoma cell line A549 (lane g) and melanoma cell line G361 (lane h), albeit at different levels.

Figure 4:
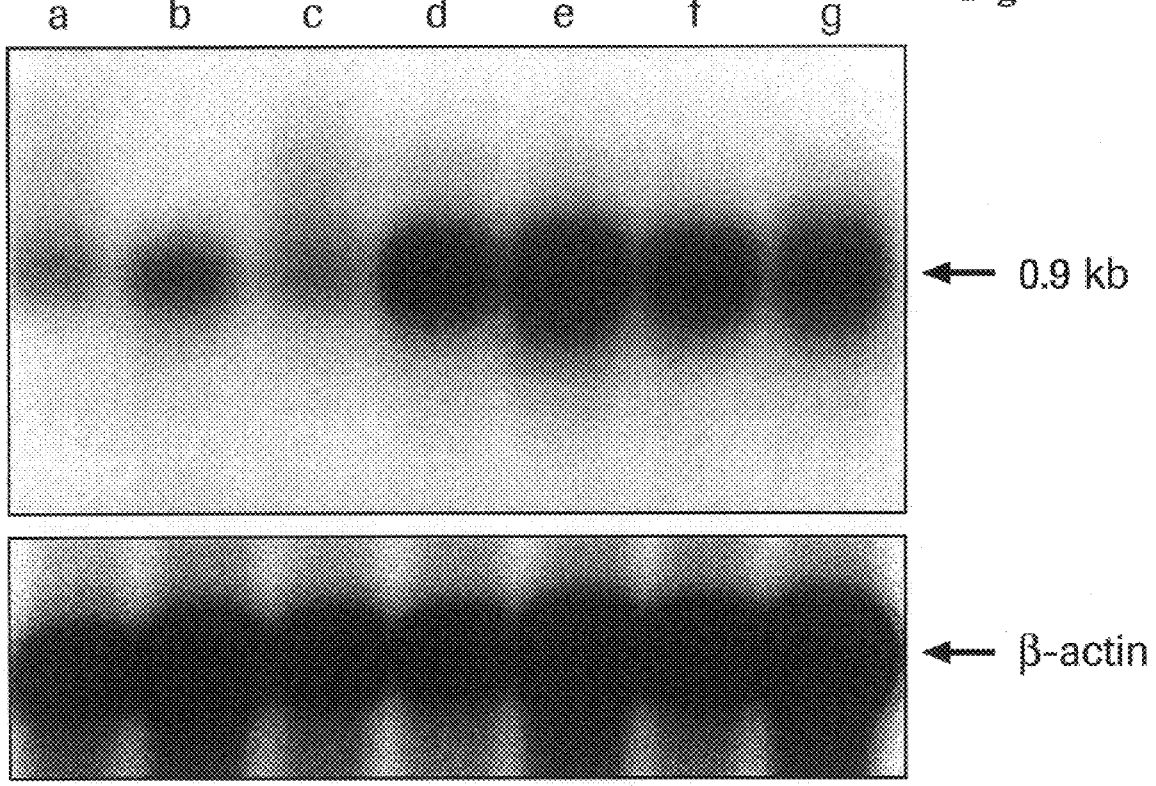
FIG. 4 Expression of URIM mRNA in cell lines derived from primary mammary carcinoma and micrometastasis. Northern Blot analysis was performed by isolating poly A+ RNA from the different cell lines, electrophoresis on a denaturing 1% formaldehyde-agarose gel, transfer to a positively charged Nylon membrane and hybridization to a $^{32}$P-labelled fragment covering the 3' coding region of URIM cDNA (SEQ ID NO:7). Equal loading with RNA was shown by hybridization to a β-actin probe.

As shown in FIG. 4, only low steady-state levels of URIM mRNA were found in normal epithelial cells derived from mammary gland (lane a), two cell lines derived from primary mammary carcinoma (lanes b and c) in contrast to three cell lines derived from bone marrow micrometastasis of mammary carcinoma (lanes d, e and g) and a metastasizing mammary carcinoma cell line derived from ascites fluid (lane g). Steady-state levels of URIM mRNA were increased up to 17 fold. These cell lines are derived from different patients (no matching between primary and micrometastasis derived cell lines). These observations indicate that expression of URIM also correlates with metastasis in mammary carcinoma.
Human Melanoma Cell Lines Cell line 530 was derived from a surgically removed human melanoma metastasis as described previously (van Muijen, G. N. P., et al., Clin. Exp. Metastasis 9 (1991) 259–272; Versteeg, R., et al., EMBO Journal 7 (1988) 1023–1029). Cell line NMCL-1 was also derived from a human cutaneous melanoma metastasis. Both cell lines were grown as monolayers in culture flasks on Dulbecco's modified Eagle medium supplemented with 10% fetal calf serum, glutamine, penicillin G and streptomycin. To determine tumorigenic and metastatic capacity of the 530 and NMCL-1 cell lines, tumor cells were harvested from subconfluent cultures by 2 min treatment with 0.25% trypsin and 0.02% EDTA. After washing with serum-containing medium cells were suspended in PBS and 5×10$^6$ cells were subcutaneously (s.c.) inoculated into the lateral thoracic wall of BALB/c athymic nude mice. Mice were inspected twice a week for local tumor growth and general condition.

For each cell line two groups of five mice were injected. Mice were killed when signs of illness or respiratory distress were noted. Mice that remained healthy were killed 3–4 months after inoculation. For detection of lung metastases microscopic inspection was performed on paraffin sections from at least 3 different levels of the lungs.

Cell line 530 showed tumor take in 8 out of 10 mice inoculated. After microscopic inspection of the lungs no metastases were found in any of these mice .

Cell line NMCL-1 showed s.c. tumor growth in all 10 mice inoculated. In contrast to cell line 530, the NMCL-1 cell line showed extensive lung metastases in all mice inoculated with this cell line.
Differential Display PCR Differential Display Polymerase chain reaction (DD-PCR) was performed following the method described by Liang and Pardee (Liang, P., and Pardee, A. B., Science 257 (1992) 967–970; Liang, P., et al., Cancer Res. 52 (1992) 6966–6968; Liang, P., et al., Nucleic Acids Res. 21 (1993) 3269–3275) using the RNA image kits (GenHunter Corp., Brookline, Mass.) according to the manufacturer's recommendation.

Total RNA was isolated from 530 and NMCL-1 cells by using RNeasy Midi Kit (Qiagen). Elimination of contaminating traces of DNA from total RNA sample was performed by digestion at 37° C. for 30 min with RNase-free DNase I using the MessageClean Kit (GenHunter Corp., Brookline, Mass.).

DNA-free total RNA (0.2 $\mu$g) from 530 and NMCL-1 cells was used as a template for first strand cDNA synthesis in the presence of 3 different one-base anchored H-T$_{11}$M primer, 1x reverse transcriptase buffer [125 mM Tris-Cl, pH 8.3, 188 mM KCl, 7.5 mM MgCl$_2$, 25 mM dithiothreitol (DDT)] and 250 $\mu$M dNTP mix. The solution was heated to 65° C. for 5 min and cooled to 37° C. for 10 min, and then 200 units of Moloney murine leukemia virus (MMLV) reverse transcriptase was added. After incubation at 37° C. for 1 h, the reaction was terminated by incubation at 75° C. for 5 min. The PCR procedure was performed in solution containing 0.1 volume of reverse transcription reaction mixture, 10 $\mu$M of the respective one-base anchored H-T$_{11}$M primer, 2 $\mu$M arbitrary 13-mer primer, 1x PCR buffer [100 mM Tris-Cl, pH 8.4, 500 mM KCl, 15 mM MgCl$_2$, 0.01% gelatin], 25 $\mu$M dNTP, 10 $\mu$Ci [$\alpha$-$^{35}$S]dATP, and 10 units of AmpliTaq DNA polymerase (Perkin Elmer, Norwalk, Conn.). PCR included a total of 40 cycles at 94° C. for 30 s, 40° C. for 2 min, 72° C. for 30 s, and finally 5 min at 72° C.

After adding 2 $\mu$l loading buffer to 3.5 $\mu$l of each sample, the PCR products were heated at 80° C. for 2 min and then loaded on a denaturing 5% polyacrylamide sequencing gel for electrophoresis. The dried gel was exposed to Kodak BioMax MR film for 48 h at room temperature and the autoradiogram was analysed with respect to differentially expressed genes. The reaction displaying unique fragments in one of the two cell lines was subsequently confirmed by repeating reverse transcription and PCR.

Unique bands reproducibly displayed in two independent DD-PCR reactions were excised from the dried gel and the cDNA was eluted from the gel by soaking the gel slice in 100 $\mu$l of H$_2$O for 10 min and then boiling for 15 min. The cDNA was recovered by ethanol precipitation in the presence of 3 M NaOAc and 50 $\mu$g glycogen as carrier and redissolved in 10 $\mu$l of H$_2$O. Four $\mu$l of eluted cDNA was reamplified in a second PCR using the same 5'- and 3'-primers and conditions described above except for dNTP concentrations of 20 $\mu$M and no radioisotope was included. The amplified PCR fragments obtained were analysed on a 1.5% agarose gel, then purified using the QIAquick Gel Extraction kit (Qiagen, Hilden) and used as probes for Northern analysis.

Northern Blot Analysis

Poly A$^+$ RNA was isolated from total RNA using the Oligotex mRNA Mini Kit (Qiagen). Parallel lanes of poly A$^+$ RNA from 530 and NMCL-1 cells (1 $\mu$g of each cell line) were size-separated on a denaturing 1% agarose formaldehyde gel and then transferred to positively charged nylon membrane (Roche Diagnostics GmbH, Mannheim) by capillary blotting in 20xSSC (3 M NaCl, 0.3 M Na$_3$citrate 2H$_2$O, pH 7.0). After UV-crosslinking (Stratagene UV Stratalinker 1800) blots were hybridized to [$\alpha$-$^{32}$P]dCTP-labelled DD-PCR products prepared by random hexamer priming and labelled to a specific activity of 2x10$^8$ dpm/$\mu$g using the Rediprime DNA labelling system (Amersham, Braunschweig). Prehybridization (0.5 h) and hybridization with radioactive probes over-night were performed in ExpressHybT™ Hybridization Solution (Clontech) at 68° C. Membranes were washed in solution 1 (2xSSC, 0.05% SDS) at room temperature for 30–40 min with continuous agitation and several replacements, specifically three replacements, of the wash solution 1 followed by a washing step with solution 2 (0.1xSSC, 0.1% SDS) at 50° C. for 40 min with one change of fresh solution. The membranes were then exposed to Cronex, Medical X-Ray Films (Sterling Disgnostic Imaging Inc., USA) at −80° C. for 48 to 72 h.

Equal loading and transfer of mRNA to the membrane was assessed by hybridizing the blots with $^{32}$P-labelled $\beta$-actin cDNA.

Cloning of DD-PCR Fragments

Northern analysis was first performed using hybridization probes generated directly from PCR reamplification. Those amplified PCR fragments detecting differentially expressed mRNAs on a Northern blot were subcloned into the pCR 2.1-TOPO vector by the Topo TA Cloning system (Invitrogen, San Diego, Calif.). Subcloned fragments were isolated using the Qiagen plasmid kit (Qiagen, Hilden) and again used as probes for Northern analysis to verify differential expression.

DNA Sequencing of Subcloned DD-PCR Fragments

Those subcloned fragments corresponding to mRNAs with differential expression were sequenced directly after subcloning into the Topo TA cloning vector (see above) using the Dye Terminator Cycle Sequencing kit (Applied Biosystems, Foster City, Calif.).

The nucleotide sequence data were analyzed for homologies with known genes in the DNA data bases using the computer programs BLAST and FASTA.

5' RACE PCR

To identify the 5'-extended region of the cDNA showing differential mRNA expression in NMCL-1 cells a 5' RACE (Rapid Amplification of cDNA Ends) PCR (Frohmann, M. A., PCR Meth. Appl. 4 (1994) 40–48; Frohmann, M. A., et al., Proc. Natl. Acad. Sci. USA 85 (1988) 8998–9002) was performed following the manual as described in the 5'RACE System for Rapid Amplification of cDNA Ends Kit, Version 2.0 (Gibco BRL, Life Technologies). First strand cDNA synthesis was synthesized from poly(A)$^+$ RNA using the gene-specific primer GSP1 (GGATCTTCCTTT TCA (SEQ ID NO:3)) and SuperScript™ II, an RNase H$^-$ derivative of the Moloney Murine Leukemia Virus Reverse Transcriptase (M-MLV RT). Following cDNA synthesis, the first strand product was purified from unincorporated dNTPs and GSP1. TdT (Terminal deoxynucleotidyl transferase) was used to add homopolymeric tails to the 3' ends of the cDNA. Tailed cDNA was then amplified by PCR using a nested, gene-specific primer GSP2 (CTCTCAGGGGCAGCATGTTA (SEQ ID NO:4)), which anneals 3' to GSP1 and the deoxyinosine-containing anchor primer AUAP (GGCCACGCGTCGACTAGTAT (SEQ ID NO:5)).

The obtained 5' RACE PCR product was cloned and sequenced.

Multiple Tissue Northern Blots

To examine the tissue-specific expression of URIM, the distribution of URIM mRNA in different human tissues was analyzed by Northern blot analysis using Multiple Tissue Northern blots (Clontech, Palo Alto, Calif.). The MTN blots containing size-fractionated mRNA extracted from various human tissues were probed with $^{32}$P-labelled URIM cDNA probe derived from the 3'-untranslated region (SEQ ID NO:7).

Equal loading of mRNA was verified by rehybridizing the MTN blots with $^{32}$P-labeled $\beta$-actin cDNA.

What is claimed is:

1. An isolated nucleic acid which is upregulated in metastatic tumor cells, consisting essentially of:
    (a) a sequence of SEQ ID NO: 1; or
    (b) a nucleic acid which, because of the degeneracy of the genetic code, is not a sequence of (a), but which codes for a polypeptide having exactly the same amino acid sequence as a polypeptide encoded by a sequence of (a).

2. The nucleic acid according to claim 1, consisting essentially of a sequence of SEQ ID NO:1.

3. An isolated nucleic acid consisting essentially of a sequence of SEQ ID NO:7.

4. An isolated nucleic acid consisting essentially of a sequence of SEQ ID NO:6.

* * * * *

SEQUENCE LISTING

<160> NUMBER OF SEQ ID NOS: 7

<210> SEQ ID NO 1
<211> LENGTH: 755
<212> TYPE: DNA
<213> ORGANISM: Homo sapiens
<220> FEATURE:
<221> NAME/KEY: CDS
<222> LOCATION: (11)..(631)

<400> SEQUENCE: 1

```
gagggtagcc atg acg gcc tcc gtg ctg cga agt atc tcg cta gcc ctg         49
           Met Thr Ala Ser Val Leu Arg Ser Ile Ser Leu Ala Leu
             1               5                  10 cgc ccg act agc ggg ctt ctg gga act tgg cag acg cag ctt aga gag         97
Arg Pro Thr Ser Gly Leu Leu Gly Thr Trp Gln Thr Gln Leu Arg Glu
         15                  20                  25 act cac cag cga gcg tca ttg ttg tct ttc tgg gaa ctc att ccc atg        145
Thr His Gln Arg Ala Ser Leu Leu Ser Phe Trp Glu Leu Ile Pro Met
 30                  35                  40                  45 aga tca gaa cct ctt cga aaa aag aag gta gat cct aaa aaa gac            193
Arg Ser Glu Pro Leu Arg Lys Lys Lys Val Asp Pro Lys Lys Asp
                 50                  55                  60 caa gaa gca aag gag cgc ttg aaa agg aag atc cga aaa ctg gaa aag        241
Gln Glu Ala Lys Glu Arg Leu Lys Arg Lys Ile Arg Lys Leu Glu Lys
             65                  70                  75 gct act caa gag cta att cct att gaa gat ttt att acc cct cta aag        289
Ala Thr Gln Glu Leu Ile Pro Ile Glu Asp Phe Ile Thr Pro Leu Lys
         80                  85                  90 ttc ttg gat aaa gca aga gag cgg cct cag gtg gag ctc acc ttt gag        337
Phe Leu Asp Lys Ala Arg Glu Arg Pro Gln Val Glu Leu Thr Phe Glu
 95                 100                 105 gag act gag agg aga gct ctg ctt ctg aag aag tgg tcc ttg tac aag        385
Glu Thr Glu Arg Arg Ala Leu Leu Leu Lys Lys Trp Ser Leu Tyr Lys
110                 115                 120                 125 cag caa gag cgt aag atg gag agg gac acc atc agg gct atg cta gaa        433
Gln Gln Glu Arg Lys Met Glu Arg Asp Thr Ile Arg Ala Met Leu Glu
                130                 135                 140 gcc cag cag gaa gct ctg gag gaa ctg caa ctg gaa tcc ccg aag ctc        481
Ala Gln Gln Glu Ala Leu Glu Glu Leu Gln Leu Glu Ser Pro Lys Leu
            145                 150                 155 cat gct gag gcc atc aag cgg gat cct aac ctg ttc ccc ttt gag aag        529
His Ala Glu Ala Ile Lys Arg Asp Pro Asn Leu Phe Pro Phe Glu Lys
        160                 165                 170 gaa ggg cca cat tac aca cca ccg atc cct aac tac caa ccc cct gaa        577
Glu Gly Pro His Tyr Thr Pro Pro Ile Pro Asn Tyr Gln Pro Pro Glu
    175                 180                 185 ggc agg tac aat gac atc acc aag gtg tac aca caa gtg gag ttt aag        625
Gly Arg Tyr Asn Asp Ile Thr Lys Val Tyr Thr Gln Val Glu Phe Lys
190                 195                 200                 205 aga tag acttgcaggc tgctatcctt aacatgctgc ccctgagagt aggaatgacc         681
Arg agggttcaag tctgccttcc acagaatcag gcatgctgtt aataaatctg gtttaatcaa      741
aaaaaaaaag cttc                                                        755
```

<210> SEQ ID NO 2
<211> LENGTH: 206
<212> TYPE: PRT
<213> ORGANISM: Homo sapiens

<400> SEQUENCE: 2

```
Met Thr Ala Ser Val Leu Arg Ser Ile Ser Leu Ala Leu Arg Pro Thr
  1               5                  10                  15
Ser Gly Leu Leu Gly Thr Trp Gln Thr Gln Leu Arg Glu Thr His Gln
             20                  25                  30
Arg Ala Ser Leu Leu Ser Phe Trp Glu Leu Ile Pro Met Arg Ser Glu
         35                  40                  45
Pro Leu Arg Lys Lys Lys Lys Val Asp Pro Lys Lys Asp Gln Glu Ala
     50                  55                  60
Lys Glu Arg Leu Lys Arg Lys Ile Arg Lys Leu Glu Lys Ala Thr Gln
 65                  70                  75                  80
Glu Leu Ile Pro Ile Glu Asp Phe Ile Thr Pro Leu Lys Phe Leu Asp
                 85                  90                  95
Lys Ala Arg Glu Arg Pro Gln Val Glu Leu Thr Phe Glu Glu Thr Glu
                100                 105                 110
Arg Arg Ala Leu Leu Leu Lys Lys Trp Ser Leu Tyr Lys Gln Gln Glu
            115                 120                 125
Arg Lys Met Glu Arg Asp Thr Ile Arg Ala Met Leu Glu Ala Gln Gln
        130                 135                 140
Glu Ala Leu Glu Glu Leu Gln Leu Glu Ser Pro Lys Leu His Ala Glu
145                 150                 155                 160
Ala Ile Lys Arg Asp Pro Asn Leu Phe Pro Phe Glu Lys Glu Gly Pro
                165                 170                 175
His Tyr Thr Pro Pro Ile Pro Asn Tyr Gln Pro Pro Glu Gly Arg Tyr
                180                 185                 190
Asn Asp Ile Thr Lys Val Tyr Thr Gln Val Glu Phe Lys Arg
                195                 200                 205
```

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:
      Primer - GSP1

<400> SEQUENCE: 3
ggatcttcct tttca                                                15

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer GSP2

<400> SEQUENCE: 4
ctctcagggg cagcatgtta                                           20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer AUAP

<400> SEQUENCE: 5
ggccacgcgt cgactagtat                                           20

```
<210> SEQ ID NO 6
<211> LENGTH: 663
<212> TYPE: DNA
<213> ORGANISM: Artificial Sequence
<220> FEATURE:
<223> OTHER INFORMATION: Description of Artificial Sequence: Probe

<400> SEQUENCE: 6
gccatgacgg cctccgtgct gcgaagtatc tcgctagccc tgcgcccgac tagcgggctt      60
ctgggaactt ggcagacgca gcttagagag actcaccagc gagcgtcatt gttgtctttc     120
tgggaactca ttcccatgag atcagaacct cttcgaaaaa agaagaaggt agatcctaaa     180
aaagaccaag aagcaaagga gcgcttgaaa aggaagatcc gaaaactgga aaaggctact     240
caagagctaa ttcctattga agattttatt acccctctaa agttcttgga taaagcaaga     300
gagcggcctc aggtggagct caccttgag gagactgaga ggagagctct gcttctgaag      360
aagtggtcct tgtacaagca gcaagagcgt aagatggaga gggacaccat cagggctatg     420
ctagaagccc agcaggaagc tctggaggaa ctgcaactgg aatccccgaa gctccatgct     480
gaggccatca agcgggatcc taacctgttc ccctttgaga aggaagggcc acattacaca     540
ccaccgatcc ctaactacca acccctgaa ggcaggtaca atgacatcac caaggtgtac      600
acacaagtgg agtttaagag atagacttgc aggctgctat ccttaacatg ctgcccctga     660
gag                                                                    663

<210> SEQ ID NO 7
<211> LENGTH: 354
<212> TYPE: DNA
<213> ORGANISM: Artificial Sequence
<220> FEATURE:
<223> OTHER INFORMATION: Description of Artificial Sequence: Probe

<400> SEQUENCE: 7
taagatggag agggacacca tcagggctat gctagaagcc cagcaggaag ctctggagga      60
actgcaactg gaatccccga agctccatgc tgaggccatc aagcgggatc ctaacctgtt     120 ccccttttgag aaggaagggc cacattacac accaccgatc cctaactacc aaccccctga    180
aggcaggtac aatgacatca ccaaggtgta cacacaagtg gagtttaaga gatagacttg     240
caggctgcta tccttaacat gctgcccctg agagtaggaa tgaccagggt tcaagtctgc     300
cttccacaga atcaggcatg ctgttaataa atctggttta atcaaaaaaa aaaa           354
```